United States Patent
Boris

(10) Patent No.: US 6,267,003 B1
(45) Date of Patent: Jul. 31, 2001

(54) METHOD FOR MEASURING CHANGES IN OSMOTIC PRESSURE

(75) Inventor: David C. Boris, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/474,151

(22) Filed: Dec. 28, 1999

(51) Int. Cl.$^7$ .................................................. G01N 13/04
(52) U.S. Cl. ............................................................ 73/64.47
(58) Field of Search ............................... 73/64.47, 61.78

(56) References Cited

U.S. PATENT DOCUMENTS

| | | | |
|---|---|---|---|
| 2,716,886 | * 9/1955 | Rowe | 73/53 |
| 3,063,288 | * 11/1962 | Reiff | 73/53 |
| 3,187,562 | * 6/1965 | Rolfson | 73/53 |
| 3,195,346 | * 7/1965 | Ehrmantraut et al. | 73/53 |
| 3,455,147 | * 7/1969 | Peck et al. | 73/64.3 |
| 3,590,634 | * 7/1971 | Pasternak et al. | 73/64.3 |
| 3,635,075 | * 1/1972 | Gilbert | 73/64.3 |
| 4,150,564 | 4/1979 | Barlow et al. | |
| 4,475,556 | * 10/1984 | Reiff | 128/673 |
| 4,706,495 | * 11/1987 | Steudle et al. | 73/64.3 |
| 4,860,577 | * 8/1989 | Patterson | 73/64.3 |
| 4,891,968 | * 1/1990 | Steudle et al. | 73/64.3 |
| 5,005,403 | * 4/1991 | Steudle et al. | 73/64.3 |
| 5,198,109 | * 3/1993 | Hansen et al. | 210/321.75 |
| 5,659,130 | * 8/1997 | Chung et al. | 73/64.47 |

OTHER PUBLICATIONS

D. C. Rau, & V. A. Parsegian, Direct Measurement Of Temperature–Dependent Solvation Forces Between DNA Double Helixes, Biophys. J. 1992, 61 (1) pp. 260–271.

N. Y. Sidorova & D. C. Rau, Removing Water From An EcoRI–Noncognate DNA Complex With Osmotic Stress, J. Biomol. Struct. Dyn. 1999, 17 (1) pp. 19–31.

* cited by examiner

Primary Examiner—Hezron Williams
Assistant Examiner—Charles D. Garber
(74) Attorney, Agent, or Firm—Mark G. Bocchetti

(57) ABSTRACT

A method is provided which allows for monitoring changes in osmotic pressure of a sample as a function of time and/or temperature. This is accomplished by placing a sample of a solution at an initial temperature into the sample cell above the membrane supported in the sample cell; sealing the sample in the sample cell; introducing gas at an elevated pressure to the sample cell to generate a dialyzate by allowing a portion of the solution to dialyze through the membrane; varying the elevated pressure of the gas until equilibrium across the membrane is substantially achieved; changing the temperature of the solution over time; measuring the osmotic pressure at predetermined intervals of time; and calculating the changes in the osmotic pressure. Alternatively, the method for monitoring changes in osmotic pressure of a sample (wherein the changes are the result of a chemical reaction generated in the sample cell) can be practiced by placing a sample of a solution at an initial temperature into a sample cell above a membrane supported in the sample cell; adding reactants to the sample; sealing the sample and reactants in the sample cell; introducing gas at an elevated pressure to the sample cell to generate a dialyzate by allowing a portion of the solution to dialyze through the membrane; varying the elevated pressure of the gas until equilibrium across the membrane is substantially achieved; measuring the osmotic pressure at predetermined intervals of time; and calculating the changes in the osmotic pressure.

22 Claims, 3 Drawing Sheets

METHOD FOR MEASURING CHANGES IN OSMOTIC PRESSURE

CROSS-REFERENCE TO RELATED APPLICATIONS

The present application is related to U.S. Application Ser. No. 09/473,071, filed Dec. 28, 1999 Herewith, by Dr. David C. Boris, and entitled, "METHOD AND APPARATUS FOR MEASURING OSMOTIC PRESSURE," and to U.S. Application Ser. No. 09/473,444, filed Dec. 28, 1999 Herewith, by Dr. David C. Boris, and entitled, "METHOD FOR DETERMINING THE CONCENTRATION OF A SOLUTION HAVING A PREDETERMINED OSMOTIC PRESSURE AND/OR GENERATING A SOLUTION WITH A PREDETERMINED OSMOTIC PRESSURE."

FIELD OF THE INVENTION

The present invention relates generally to osmometry and, more particularly, to measuring the osmotic pressure of complex solutions including, but not limited to, emulsions, dispersions, and charged and uncharged polymer solutions.

BACKGROUND OF THE INVENTION

A variety of methods and devices are known for measuring the osmotic pressure exerted by solvent molecules diffusing through a semipermeable membrane. Commercially available devices for measuring the osmolality of solutions via membrane osmometry include the 4400 series colloid osmometers made by WesCor (Logan, Utah) and the type 1.00 Knaur membrane osmometers. Other devices for measuring the osmolality of solutions through vapor pressure osmometry are commercially available. An example of this type of device is the VPO model 070 made by UIC Inc. (Joliet, Ill.). Still another known osmometer device operates by measuring freezing point depression. An example of this type of device is the Precision Systems Inc. (Natick, Mass.) Osmette XL product line. Other known osmometer variants include isopiestic vapor equilibrium osmometers and submerged dialysis bag osmometers. In addition, osmolality has been determined by measuring boiling point elevation. The vapor pressure osmometer, boiling point elevation, freezing point depression, and isopiestic methods measure the oncotic pressure (the osmotic pressure exerted by colloid in the solution) of the solution, that is, the osmolality of the solution including the contribution of low molecular weight components such as salts. The present invention is directed to methods for measuring the osmotic pressure of solutions, excluding the contribution of small molecules.

Membrane osmometers and the dialysis bag techniques measure the solution equilibration across a semi-permeable membrane, thus excluding the direct contribution of small permeable molecules. One example of a membrane osmometer is taught in U.S. Pat. No. 4,150,564, titled "OSMOMETER FOR COLLOID OSMOMETRY," by Wayne K. Barlow, et al., Apr. 24, 1979. The present invention is an improvement upon existing membrane osmometer designs, but relies on the same basic principle of establishing an equilibrium across a semi-permeable membrane. Typical membrane osmometers employ pressure transducer technology to directly measure the evolved osmotic pressure difference between a reference cell and the sample solution across a semi-permeable membrane. In the present invention, transducer technology is not required for measuring the osmotic pressure. Typical commercial osmometers are designed to minimize the sample volumes by introducing the sample into a meandering channel above the semi-permeable membrane that maximizes surface contact while minimizing sample volume. This meandering channel geometry is eliminated in the present invention because it limits the usefulness of commercial osmometers to low viscosity, non-fouling solutions and is particularly unsuited for complex solutions (dispersions and emulsions).

Dialysis bag techniques, (Essafi, W. *Structure Des Polyelectrolytes Fortement Charges*, PhD thesis, Universite Pierre et Marie Curie, Paris, 1996) involve filling a semipermeable dialysis bag with the sample solutions of unknown osmotic pressure and immersing it in a large volume of solution of known osmotic pressure. The sample changes concentration until an osmotic equilibrium is established. Then the sample is removed and its concentration at that known osmotic pressure is determined using other techniques (spectrophotometrically or gravimetrically). The present invention may be used in a mode of operation similar to this. In this mode of operation the sample solution is allowed to equilibrate to a known imposed air pressure. Then the concentrated sample is removed and the concentration determined separately. However, this method of operation is not the optimal nor is it the preferred embodiment of the method of the present invention.

The prior art also suggests use of polymer solutions of known osmotic pressure to have as reference solutions (rather than solvent) using commercial osmometers or other direct force measurement techniques to allow for measurement of higher osmotic pressure solutions, (Rau, Donald C.; Parsegian, V. Adrian. *Direct Measurement Of Temperature-Dependent Solvation Forces Between DNA Double Helixes*. Biophys. J. (1992), 61(1), 260–71; Sidorova, Nina Y.; Rau, Donald C. *Removing Water From An EcoRI-noncognate DNA Complex With Osmotic Stress*. J. Biomol. Struct. Dyn. (1999), 17(1), 19–31). This method works reasonably well for extending the pressure range available on commercial osmometers but does not properly treat the Donnan equilibrium established for charged species thereby potentially leading to erroneous results with charged polymers. This method of extending the pressure range is not needed in the operation of the present invention as the reference solution is simply dialyzate.

The present invention capitalizes upon advances in stirred cell dialysis chamber technology to improve osmometer design. Stirred cell dialysis chambers are available from, for example, Amicon (Beverly, Mass.). The principal use of the dialysis chamber in the prior art is to either concentrate a sample solution or to remove small molecule impurities by exhaustive flushing with pure solvent. The stirred cell is designed to be dismantled easily for cleaning. It has a magnetic stirring rod suspended above the membrane to keep the solution well stirred and to sweep clean the surface of the membrane. It can withstand more than 75 psi of external pressure, far exceeding the pressure measurable in conventional membrane osmometers (~1–3 psi).

SUMMARY OF THE INVENTION

It is therefore an object of the present invention to provide a method for measuring changes in osmotic pressure of a solution over time.

A further object of the present invention is to provide a method for measuring changes in osmotic pressure which includes stirring the sample to sweep the surface of the membrane continually thereby reducing surface fouling and removing bubbles that hamper the accuracy and reliability of prior art osmometers when used to measure complex fluids.

Yet another object of the present invention is to provide a method which keeps the sample well mixed thereby avoiding particle settling and the development of surface concentration gradients.

It is a further object of the present invention to provide a method for measuring changes in osmotic pressure which can make such measurements more quickly than then conventional prior art osmometers.

It is yet another object of the present invention to provide a method and apparatus for measuring osmotic pressure which does not require multiple flushes of each sample solution before concentrations stop changing (as a result of dilution of the sample reservoir due to equilibration with the reference reservoir) and the results are reproducible.

Still another object of the present invention is to provide a method which can be used for measuring osmotic pressure of high viscosity solutions (above about 100 cp).

The foregoing and numerous other features, objects and advantages of the present invention will become readily apparent upon reviewing the detailed description, claims and drawings set forth herein. These features, objects and advantages are accomplished by providing a sample cell with a removable pressurizing lid through which a sample solution may be introduced into the chamber of the sample cell. The sample is introduced above a membrane residing in the sample cell with a meandering dialyzate cell positioned below the membrane. Pressurized gas is introduced into the sample cell via a pressure regulator. Once the sample is forced through the membrane and dialyzate begins to emerge through a transparent dialyzate tube from the meandering dialyzate cell, the pressure through the pressure regulator is reduced until flow ceases. A magnetic stirrer is used to continually sweep the surface of the membrane. The primary purposes of the meandering dialyzate cell are to provide a structure for collecting dialyzate with maximum surface area contact with the membrane (for fast equilibration with the sample cell) which minimizes the volume of dialyzate relative to the volume of sample in the sample cell. However, those skilled in the art will recognize that the present invention can be practiced without a meandering dialyzate cell. Instead, the sample cell can easily be provided with a support structure other than a meandering dialyzate cell to support the membrane therein. Similarly, the sample cell can also be provided with a different dialyzate collector (e.g. a funnel). The support structure for the membrane and the dialyzate collector do not have to be integrated as is the case with a meandering dialyzate cell. However, these alternative arrangements would likely (although not necessarily) increase the volume of dialyzate needed before a meniscus is achieved in the transparent dialyzate exit tube.

The use of a pressure regulator and an accurate pressure gauge allow for precise control and measurement of the applied air pressure on the sample. By systematically varying the applied air pressure until the visually observed liquid meniscus of the dialyzate in the dialyzate tube is stationary, the osmotic pressure of the solution across the dialysis membrane is exactly balanced by the imposed air pressure. Further, the method and apparatus of the present invention allow for the progressive adding of known amounts of diluent to the sample solution and mixing the new dilutions directly in the sample cell. This is achieved practically by simply placing the entire cell on an accurate balance and weighing the amount of added solution before each osmotic measurement. Calibration of the apparatus of the present invention does not require equilibration of a sample. Rather, calibration is a simple and fast procedure based on accurately measuring the air-line pressure. This is in marked contrast to the difficulty of repeatedly calibrating transducers and properly seating membranes in prior art membrane osmometers. This leads to a significant advantage in the amount of time required to operate the apparatus.

Specifically, the method of the present invention allows for monitoring changes in osmotic pressure of a sample as a function of time and/or temperature. This is accomplished by placing a sample of a solution at an initial temperature into the sample cell above the membrane supported in the sample cell; sealing the sample in the sample cell; introducing gas at an elevated pressure to the sample cell to generate a dialyzate by allowing a portion of the solution to dialyze through the membrane; varying the elevated pressure of the gas until equilibrium across the membrane is substantially achieved; changing the temperature of the solution over time; measuring the osmotic pressure at predetermined intervals of time; and calculating the changes in the osmotic pressure. Alternatively, the method for monitoring changes in osmotic pressure of a sample (wherein the changes are the result of a chemical reaction generated in the sample cell) can be practiced by placing a sample of a solution at an initial temperature into a sample cell above a membrane supported in the sample cell; adding reactants to the sample; sealing the sample and reactants in the sample cell; introducing gas at an elevated pressure to the sample cell to generate a dialyzate by allowing a portion of the solution to dialyze through the membrane; varying the elevated pressure of the gas until equilibrium across the membrane is substantially achieved; measuring the osmotic pressure at predetermined intervals of time; and calculating the changes in the osmotic pressure.

For improved accuracy the height of both the dialyzate liquid column in the dialyzate tube and the sample reservoir are recorded and used to correct for the known hydrostatic pressure difference. The entire apparatus is placed on a hot plate for temperature control. This method is very fast, approximately 4–50 times faster than other methods. Because of the speed of measurement of the present invention, the osmotic pressure of chemical reactions can be monitored as a function of time or temperature in the sample cell. This feature potentially opens new areas of research for instance in medicine, or polymer chemistry where the appearance or disappearance of reactants is accompanied by an osmotic pressure change.

DESCRIPTION OF THE PREFERRED EMBODIMENT

Figure 1:
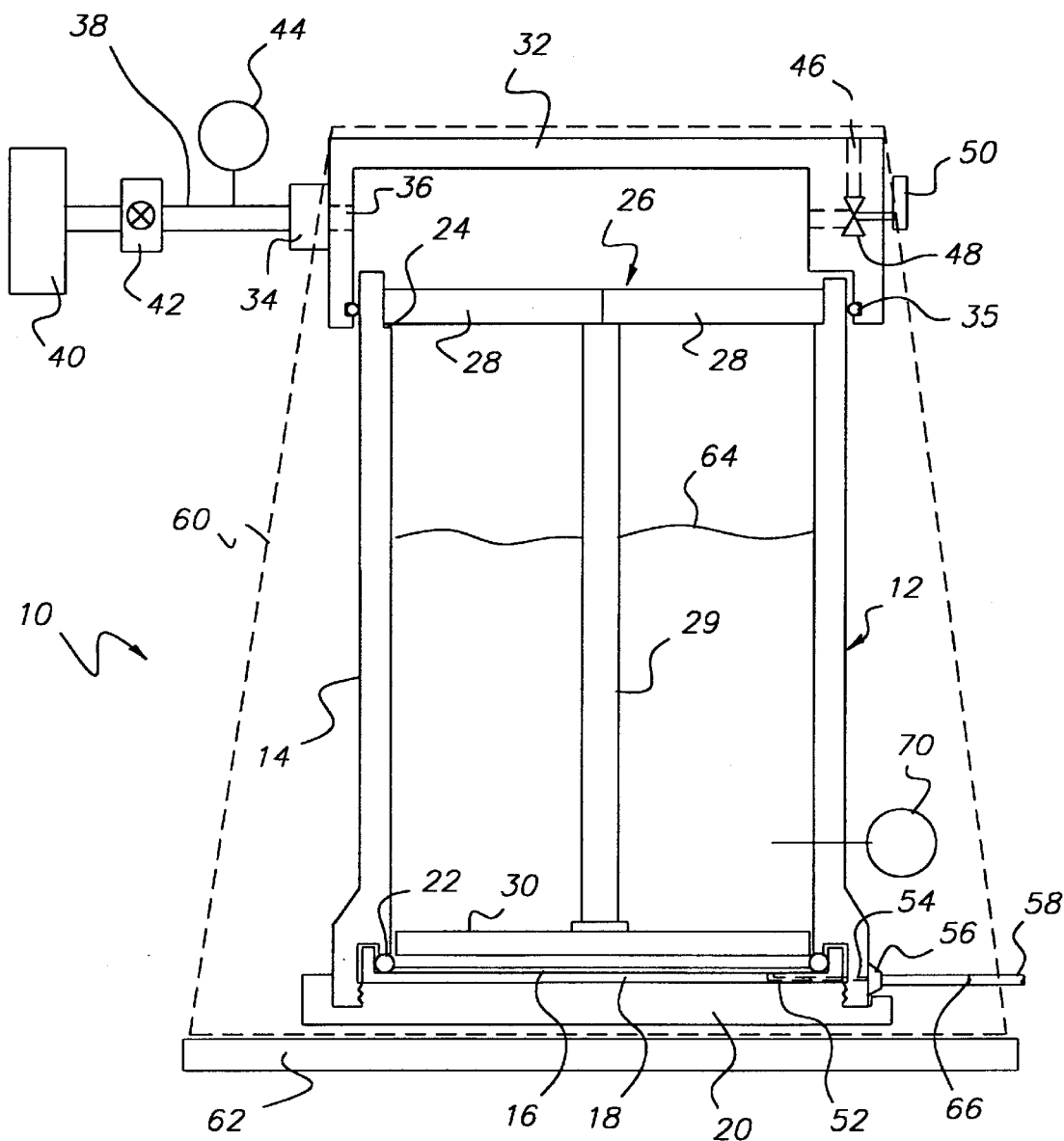
FIG. 1 is a schematic cross-sectional view of the osmometer device of the present invention.

Turning first to FIG. 1 there is shown a schematic perspective view of the osmometer 10 of the present invention.

The osmometer 10 includes a sample cell 12. Sample cell 12 includes a chamber body 14 which is preferably made of polysulfone and is preferably transparent. An Amicon 8400 stirred cell dialysis chamber serves well as sample cell 12. Residing in chamber body 14 is membrane 16. Many semi-permeable membranes are available commercially which work well. For aqueous solutions a Diaflo ultrafiltration membrane YM10 (10K Mw cut-off) was effectively used for membrane 16. Other membranes could be chosen with tighter (or looser) pores to selectively measure the osmotic contribution of lower (or higher) molecular weight fractions of the sample solution. Many of the commercially available membranes are suitable for organic solvents. Many of the commercially available membranes are suitable for organic solvents. The Diaflo YM10 membrane is suitable for most organic solvents as well, excluding Amines, phenols and solutions with pH less than 3 or greater than 13. This is not a limitation of the device, other membranes are commercially available which circumvent all of these limitations. Membrane 16 is supported on meandering dialyzate cell 18. Meandering dialyzate cell 18 is retained in chamber body 14 by means of base plate 20 which threadably engages chamber body 14. An O-ring 22 provides a seal between chamber body 14 and meandering dialyzate cell 18. There is a circumferential lip 24 in the interior surface of chamber body 14. Circumferential lip 24 provides residence for support bracket 26 which preferably includes three radial spokes 28. Extending down from support bracket 26 is stir rod axle 29. Rotatably mounted on stir rod axle 29 is stir rod blade 30.

Press fit onto the top of chamber body 14 is lid 32. A seal between lid 32 and chamber body 14 is provided by means of O-ring 35. Attached to lid 32 is bushing 34 which aligns with bore 36 in lid 32. Extending from bushing 34 is pressurized gas conduit 38 for which pressurized gas is supplied from a pressurized gas source 40. Mounted in pressurized gas conduit 38 is a pressure regulator 42 and a pressure gauge 44. Lid 32 is also provided with an L-shaped bore 46 in which a pressure relief valve 48 is mounted. Pressure relief valve 48 is manually operated by means of handle 50.

Figure 2:
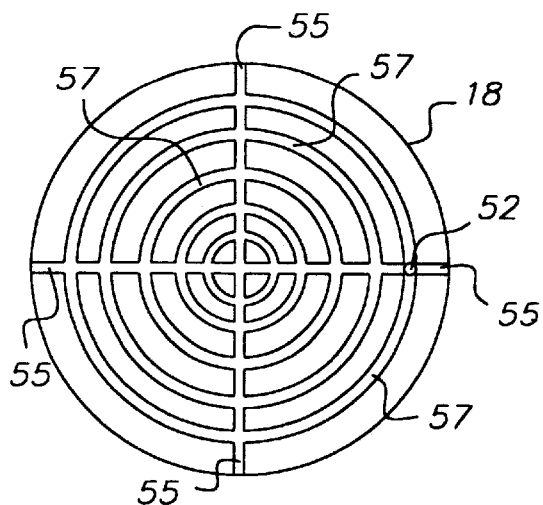
FIG. 2 is a top plan view of the meandering dialyzate cell.

There is a bore 52 into meandering dialyzate cell 18 which communicates with one of radial channels 55 (see FIG. 2) in the top surface of meandering dialyzate cell 18. The top surface of meandering dialyzate cell 18 also includes a series of concentric channels 57 therein in the top surface of meandering dialyzate cell 18. Bore 52 aligns with bore 54 through chamber body 14. Coupling 56 mounts to chamber body 14 at bore 54 and transparent dialyzate exit tube 58 extends therefrom.

Figure 3:
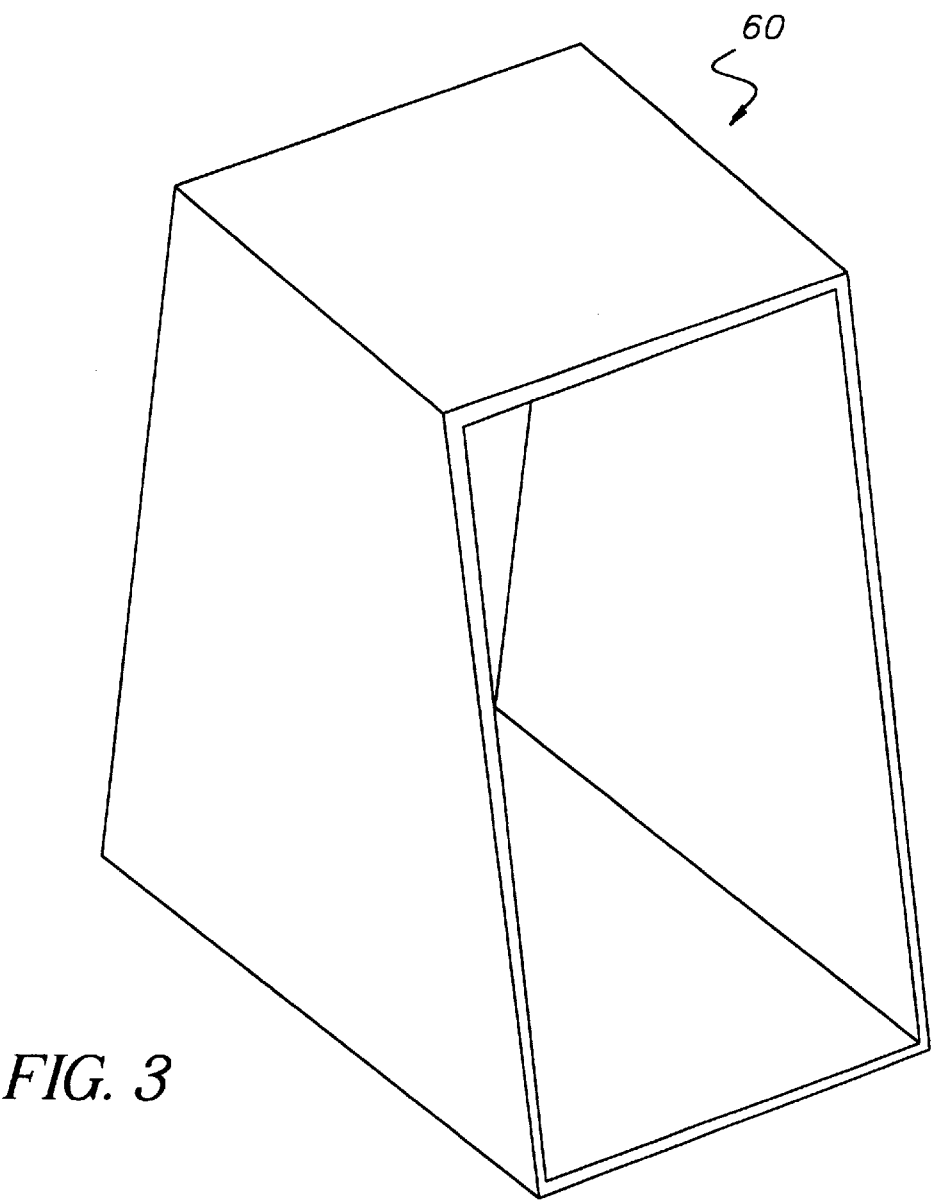
FIG. 3 is a perspective view of the frame in which the osmometer device of FIG. 1 resides during operation.

When in operation sample cell 12 resides in frame 60 (shown in a perspective view in FIG. 3) which is preferably open on at least two sides thereof to permit observation of sample cell 12. Frame 60 is made of metal (preferably steel) and insures that lid 32 is retained on chamber body 14 when sample cell 12 is pressurized via pressurized gas conduit 38. Frame 60 is supported on magnetic stirring/hot plate 62. An exemplary magnetic stining/hot plate 62 that may be used in the practice of the present invention is a Corning Hot Plate/Stirrer model PC-351. Because frame 60 is metallic, it acts as a good heat conductor for heating sample cell 12.

Initially the pressurizing lid 32 is removed and the sample solution 64 is introduced into the chamber 14 above the membrane 16. The gas delivered via pressurized gas conduit 38 can be air, nitrogen or a non-interacting (inert) gas. Preferably, pressurized gas source 40 can deliver gas at a relatively high pressure (80 psi). The air pressure applied to the sample solution 64 is controlled by the pressure regulator 42 which has the capability of smoothly varying the pressure over the entire desired range of measurement (0–10 psi for low pressure applications, 0.2–75 psi for high pressure applications). Pressure regulators with more or less sensitivity can be chosen based upon the osmotic pressure of the sample solution being measured and the desired accuracy. Two examples of pressure gauges can be used in the operation of the present invention are the Nullmatic 40–30 pressure regulator and the Ashcroft 40 psi pressure regulator. The applied pressure is measured on pressure gauge 44. The accuracy and range of the osmometer 10 depends on the accuracy and pressure range of the pressure gauge 44 selected. A Capsuhelic 0–300 inch of water gauge has been used successfully for lower pressure solutions. Additional accuracy can easily be obtained by using any of a number of more expensive and accurate commercially available pressure gauges.

The sample cell 12 plus solution 64 is weighed and then the lid 32 is sealed with the pressure release valve 48 open. The sealed sample cell 12 is then placed inside the metal pressure frame 60 and the pressure release valve 48 is closed. This frame 60 holds the lid 32 firmly in place under pressurization. The base of the frame 60 establishes good thermal contact between the magnetic stirring/hot plate 62 and the sample cell 12. The heating element of the magnetic stirring/hot plate 62 is turned on and set to the chosen temperature setting. The entire apparatus can be submerged into a water bath (not shown) with a temperature sensor (not shown) for precise temperature control. Because of the large volume of sample solution 64 and the fast measurement time this step is often not needed in the practice of the method of present invention. The magnetic stir portion of the magnetic stirring/hot plate 62 is turned on thereby magnetically driving the angled magnetic stirring rod blade 30 which is preferably set to a moderate rate of stirring of about 1–2 revolutions per second. For clear solutions the surface of the membrane 16 is then visually inspected through the transparent sides of the chamber 14 for bubbles or debris.

The pressure is raised initially to between 5 and 15 psi to wet the membrane 16 with the sample solution 64. Once the sample solution 64 is forced through the membrane 16 and the dialyzate begins to emerge through the transparent dialyzate exit tube 58 such that there is a visible meniscus 66 therein, the pressure is reduced using the pressure regulator 42 until flow ceases. Pressure is reduced further until flow reverses direction and the dialyzate is drawn back into the meandering dialyzate cell 18 and ultimately back through the membrane 16 into the transparent sample chamber 14. The meandering channel dialyzate cell 18 maximizes the surface area for equilibration while minimizing the volume of dialyzate and thus the amount of dilution of the sample 64. This is a dramatic improvement over the commercial membrane osmometers that have meandering channel sample chambers which minimize the sample volume rather than the dialyzate volume. For fast and easy use a minimum dialyzate volume to sample volume ratio is preferable. For expensive samples a smaller cell can be selected which maintains the large sample volume to dialyzate volume ratio but reduces the dimensions of the entire cell. Finally, the pressure is varied carefully until the meniscus 66 in the dialyzate exit tube 58 holds substantially stationary, that is, stationary over a few minute time period. The osmotic pressure of the sample solution 64 is equal to the applied gas pressure read upon the pressure gauge 44 when the flow is substantially stationary, that is when equilibrium across the membrane is reached. Preferably, the osmotic pressure measured is then corrected for the slight hydrostatic pressure difference calculated from the difference in height of the liquid column in the dialyzate exit tube 58, and the height of the sample surface 64 in the sample cell 12 (typically this correction is between 1 and 10 centimeters of water). This technique of measuring the hydrostatic pressure differential can be adapted into a method for achieving increased accuracy, particularly in low pressure applications (0–1 psi). Increased accuracy in low pressure applications can be accomplished by suspending the dialyzate tube vertically and measuring the difference in heights of the stationary meniscus 66 in the dialyzate tube 58, and the height of the sample surface 64 in the sample cell 12. The osmotic pressure is then calculated by correcting the gauge pressure for the hydrostatic pressure difference. Preferably, the step of measuring the difference in heights of the stationary meniscus 66 in the dialyzate tube 58, and the height of the sample surface 64 in the sample cell 12 is performed at two or three applied pressures typically differing by a few centimeters of water (1–5 cm). The osmotic pressure is then calculated by correcting the gauge pressure for the hydrostatic pressure difference for each chosen pressure. The two or three osmotic pressure values obtained are then averaged. Typically the pressures chosen are only different by a few centimeters of water to avoid large columns of dialyzate in the vertical dialyzate exit tube which would require large dialyzate volumes.

For measuring a dilution series the pressure relief valve 48 is open, the lid 32 is removed, the diluent is added and the sample is reweighed so that the new concentration is known. The lid 32 is reaffixed and put in the metallic frame 60. Finally the pressure relief valve 48 is closed and the measurement method is repeated as described above. This entire process can be performed in just a few minutes.

An alternate method of measuring the osmotic pressure of a sample solution is to set the pressurized gas conduit 38 to a fixed pressure using the pressure regulator 42 and pressure gauge 44 and then wait for the solution to dialyze down to the concentration corresponding to this pressure. The solution can then be removed and its concentration can be determined using other techniques (spectrophotometrically or gravimetrically for instance). This mode of operation allows for the preparation of solutions of known osmotic pressure. This is not the preferred mode of use because the dialysis process is quite time consuming, sometimes taking several hours to reach the chosen osmotic pressure.

Figure 4:
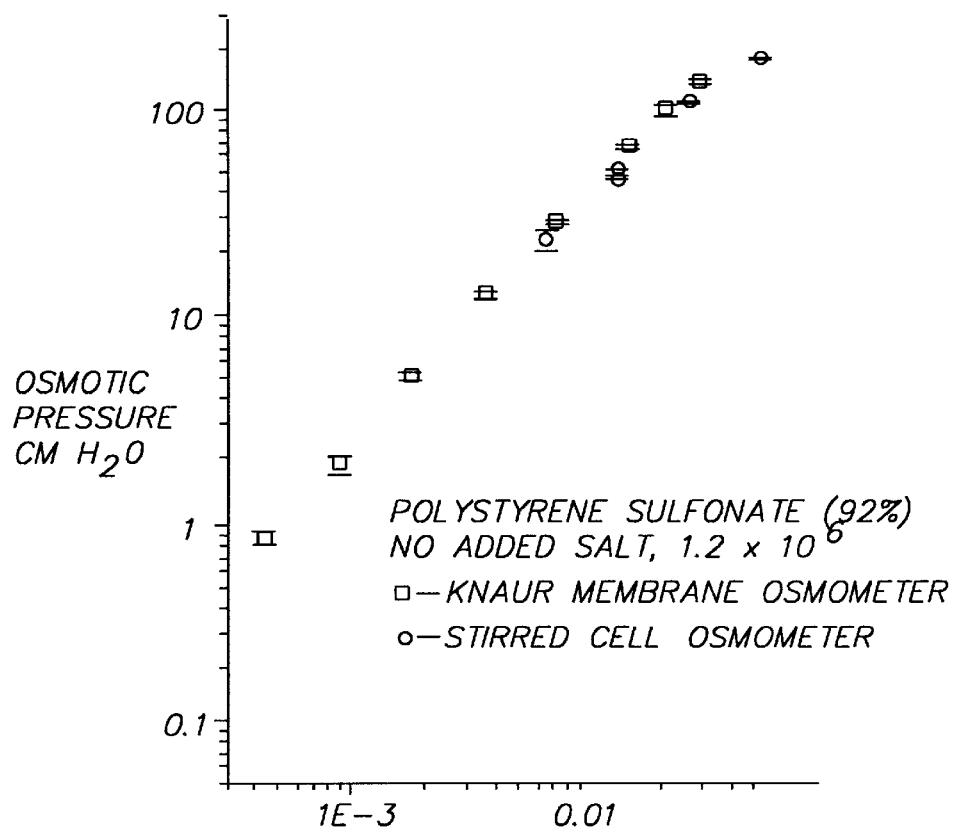
FIG. 4 is a graph showing a comparison of osmotic pressure versus concentration data on Polystyrene Sulfonate obtained using the present invention and compared directly to data using a conventional prior art membrane osmometer.

Looking next at FIG. 4, the accuracy of the present invention is demonstrated using some standard solutions from the prior art literature. Clearly the data generated using the method and apparatus of the present invention is in good agreement with the polystyrene sulfonate data measured using conventional membrane osmometry. Further, the highest concentration point obtained using the invention was beyond the viscosity and pressure range accessible using conventional membrane osmometry methods.

Figure 5:
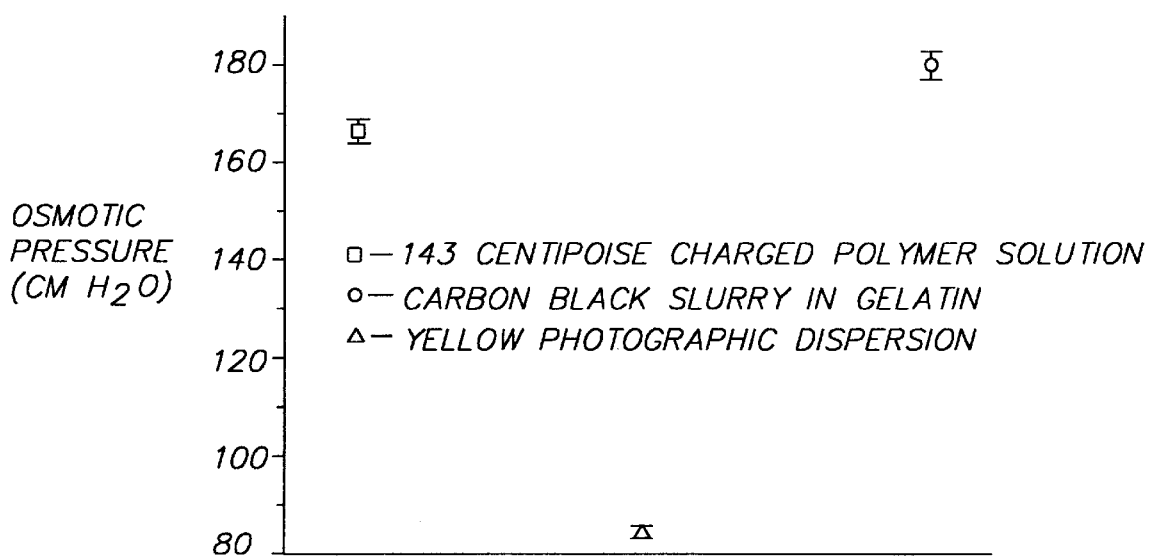
FIG. 5 plots osmotic pressure data from three complex solutions not amenable to conventional prior art osmometry techniques including a silver halide containing gelatin photographic dispersion, a carbon particle slurry and a high viscosity charged polymer solution.

Turning to FIG. 5, it can be seen that the osmotic pressure data was obtained for three complex solutions using the present invention. The osmotic pressure of these three complex solutions cannot be measured using prior art membrane osmometry techniques. The first solution is a 143 centipoise charged polymer solution made from mixing gelatin and a synthetic polyelectrolyte. This high viscosity solution cannot be measured using the meandering sample channel arrangement of commercial membrane osmometers because of the high backpressure needed to introduce the solution. In addition, this high osmotic pressure is slightly beyond the nominal operating limits of commercial membrane osmometers (although most transducers are still fairly linear in this range). The second solution is a carbon black slurry dispersed in gelatin. While the high measured osmotic pressure of this solution is slightly beyond the operating limits of conventional membrane osmometers, the more significant problem with this solution is that the introduction of such a carbon black slurry into commercial osmometers will foul the osmometer severely. The procedure for cleaning and recalibration of the osmometer after this solution requires several hours and makes these sorts of measurements time prohibitive as a practical matter. In contrast, in the operation of the present invention another solution can be measured within minutes. The third solution measured is a yellow photographic (silver halide) dispersion. This solution fouls conventional membrane osmometers and gives data which is not reproducible because of settling and surface plugging. These problems are avoided using the present invention because of the constant stirring of the solution and sweeping of the surface.

As discussed above, those skilled in the art will recognize that the present invention has many advantages over prior art osmometers. For example, it should be appreciated that the present invention is easily dismantled and cleaned so that complex fluids (emulsions and dispersions) can be measured, which would foul traditional meandering channel membrane osmometers. In addition, the magnetic stirring rod blade 30 that continually sweeps the surface of the membrane 16, reduces surface fouling and removes bubbles that hamper the accuracy and reliability of commercial prior art membrane osmometers when used to measure complex fluids. Further, because chamber body 14 of the device is transparent, the upper surface of the membrane 16 may be observed to check for detrimental bubbles, deposits, etc. In addition, the magnetic stirrer keeps the sample well mixed, avoiding particle settling and the development of surface concentration gradients which can lead to inaccurate measurements in commercial membrane osmometers of the prior art when used with complex fluids (particularly dispersions).

Sample measurements in the present invention are very fast, approximately 4–50 times faster than other prior art methods. Because of the speed of use of the present invention it can be used to measure the osmotic pressure for solutions that change as a function of time or temperature. In fact, chemical reactions can be initiated in the osmometer sample cell and then monitored as a function of time. Reactants can be added to the sample cell at the desired temperature, and a timer can be started. The sample cell 12 is sealed and placed on the magnetic stirring/hot plate 62 where the temperature is maintained and mixing is initiated. The sample cell 12 is pressurized and the pressure is varied until the dialyzate meniscus 66 in the exit tube 58 is substantially stationary, that is, there is substantial equilibrium across the membrane. The meniscus 66 may not become entirely stationary if the osmotic pressure of the reacting sample is changing too rapidly. The pressure, as read from pressure gauge 44, required to keep the meniscus 66 stationary, is then recorded as a function of time. These measurements can be recorded repeatedly at a time step as small as 1–2 minutes to monitor the evolution of a chemical (or biological) reaction that changes osmotic pressure with time. Chemical and biological reactions that change osmotic pressure with time include an enormous class of reactions that use up or produce reactants.

An alternative embodiment of the method of the present invention is to monitor the changes in osmotic pressure of a sample or ongoing chemical reaction as a function of time as the temperature is varied. This involves using a hot plate or water bath capable of varying the temperature of the sample. To measure the temperature one can affix a thermometer 70 or a thermocouple probe or other temperature sensing devices to the cell. In this case the sample (or reactants) are added at some prescribed temperature to the sample cell 12, and a timer is started. The sample cell 12 is sealed and placed on the magnetic stirring/hot plate 62 (or in the water bath) where mixing is initiated in the sample cell 12 and the temperature is varied in some predetermined way as a function of time. Examples include ramping the temperature either upward or downward, or causing step changes in the temperature of the sample 64. The sample cell 12 is pressurized and the pressure is varied until the dialyzate meniscus 66 in the exit tube 58 is nearly stationary. The meniscus 66 may not become entirely stationary if the osmotic pressure of the sample 64 is changing too rapidly. The pressure on the gauge 44 needed to keep the meniscus 66 stationary is then recorded as a function of time and temperature. This is the osmotic pressure. These measurements can be recorded repeatedly at a time step as small as 1–2 minutes to monitor the evolution of a chemical (or biological) reaction that changes osmotic pressure with temperature and time. These techniques would be particularly suitable for monitoring the progress of chemical or physical gelation reactions for example. The osmometer 10 of the present invention can clearly be used to measure the osmotic pressure of samples 64 which are unstable if held more than 5–10 minutes (for example due to chemical or colloidal instabilities) or change substantially within 5–10 minutes. Previously these types of measurements simply were not possible with commercial prior art membrane osmometers. This alternative embodiment can be used to monitor the changes in osmotic pressure of a sample as a function of time as the temperature is varied, not only for chemical reactions, but also for those changes in osmotic pressure resulting from, for example, phase changes, morphological changes, colloidal instabilities including Oswald ripening, aggregation, counter ion condensation, and micelle formation.

Sample measurements in the device of the present invention are very fast, approximately 4–50 times faster than other prior art methods. Because of the speed of use of the present invention it can be used to measure the osmotic pressure for solutions that are unstable if held more than 5–10 minutes (for example due to chemical or colloidal instabilities). Previously these measurements simply were not possible with commercial prior art membrane osmometers. The present invention is faster because the sample volume is typically several hundred times larger than the dialyzate volume so that the change in concentration upon equilibration can be safely ignored allowing accurate measurements to be made immediately (1–5 minutes per sample). In contrast, typical prior art membrane osmometers require multiple flushes of each sample solution before concentrations stop changing and reproducibility is established (~20–50 minutes per sample). A second reason that the device of the present invention allows for faster measurements is that new solutions can be mixed directly in the sample cell 12. Accurate dilution series are made by starting from a sample solution 64 and progressively adding known amounts of diluent. This is achieved practically by simply placing the entire cell on an accurate balance and weighing the amount of added solution before each measurement. This sort of mixing and weighing is not possible in conventional art osmometers and thus requires the individual preparation of separate samples for dilution series. In addition, because the sample cell 12 is not mixed in conventional prior art osmometers, between each measured dilution several extra flushes are typically required to achieve stable measurements, further slowing down the measurement process. In the operation of the present invention, calibration does not require equilibration of a sample. It is simple and fast based on accurately measuring the air-line pressure. This is in marked contrast to the difficulty of repeatedly calibrating transducers and properly seating membranes in commercial prior art membrane osmometers. This leads to significant time savings in operation.

Further, the accuracy of the device of the present invention is significantly greater than with prior art osmometers. The accuracy of the device of the present invention is determined by the air pressure gauge which can be controlled very precisely (to within millimeters of water if desired). Commercial prior art osmometers can only achieve 1–2 cm of water accuracy. The applicable pressure range which can be used in the operation of the present invention is determined by the sample cell maximum (which can withstand up to 75 psi), far higher than the conventional transducer technology used in prior art membrane osmometers which typically measure in a range of 1.5–3 psi).

Finally, the present invention enables the determination of the osmotic pressure of high viscosity solutions. Meandering channel osmometers of the prior art have small sample volumes and small sample channels and due to high back-pressure are unusable with high viscosity solutions (above about 100 cp).

In the preferred embodiment, transparent dialyzate exit tube 58 has been described herein as extending from a coupling 56 attached to the chamber body 14 at bore 54. Those skilled in the art will recognize that a variety of different structural arrangements are available for providing and attaching the transparent dialyzate exit tube 58. Transparent dialyzate exit tube 58 can even originate inside chamber body 14 so long as the meniscus can still be viewed. As such, dialyzate exit tube 58 will be attached, either directly or indirectly, to some portion of sample cell 12. The dialyzate exit tube 58 must, however, be transparent and should be oriented at any angle from horizontal to a configuration where a large portion thereof is oriented vertically upward. By vertically upward, it is meant that the dialyzate exit tube 58 can be oriented vertically with the end thereof which is open to atmosphere residing at a higher elevation than the remainder of exit tube 58.

In the description of the method and alternative methods of the present invention, the sample or solution is described as being introduced to the sample cell 12 above the membrane 16. Those skilled in the art will recognize that a variety of configurations are available for sample cell 12 which may not be in agreement with the traditional meaning of the terms "above" and "below". For example, the sample cell may take the shape of a U-shaped cylinder with the membrane positioned perpendicular to the cylindrical axis of the U-shaped cylinder almost anywhere along the length thereof. With that in mind, it is appropriate to think of the sample cell 12 being divided by the membrane 16 such that there is a sample side of the membrane 16, (that side of the membrane 16 where the sample or solution is added to the sample cell 12), and a dialyzate side of the membrane 16. For the purposes of this application "above" is intended to mean on the sample side of the membrane 16.

The present invention has far reaching potential uses. It allows for easy measurement of osmotic pressure of complex fluids and could be used as a method for screening drugs for activity in osmotically implicated biological phenomena such as blood pressure changes, arthritic swelling of joints and excessive ocular pressure. It makes possible the study of the evolution polymerization reactions, and colloidal instability phenomenon. The osmotic pressure gives a direct measure of the appearance or disappearance of macromolecular charged species. This sort of research has been hampered by the problems of commercial prior art osmometers overcome by this invention.

From the foregoing, it will be seen that this invention is one well adapted to obtain all of the ends and objects hereinabove set forth together with other advantages which are apparent and which are inherent to the invention.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth and shown in the accompanying drawings is to be interpreted as illustrative and not in a limiting sense.

PARTS LIST 10 osmometer
12 sample cell
14 chamber body
16 membrane
18 meandering dialyzate
20 base plate
22 o-ring
24 circumferential lip
26 support bracket
28 radial spokes
29 stir rod axle
30 stir rod blade
32 lid
34 bushing
35 o-ring
36 bore
38 pressurized gas conduit
40 pressurized gas source
42 pressure regulator
44 pressure gauge
46 L-shaped bore
48 pressure relief valve
50 handle
52 bore
54 bore
55 radial channels
56 coupling

Parts List—continued 57 concentric channels
58 transparent dialyzate exit tube
60 frame
62 magnetic stirring/hot plate
64 sample solution
66 meniscus
70 thermometer

What is claimed is:

1. A method for monitoring changes in osmotic pressure of a sample as a function of time comprising the steps of:
   (a) placing a sample of a solution at an initial temperature into a sample cell above a membrane supported in the sample cell;
   (b) sealing the sample in the sample cell;
   (c) introducing gas at an elevated pressure to the sample cell to generate a dialyzate by allowing a portion of the solution to dialyze through the membrane and enter a transparent dialyzate exit tube connected to sample cell;
   (d) varying the elevated pressure of the gas to obtain a substantially stationary dialyzate meniscus in the transparent dialyzate exit tube indicating osmotic pressure equilibrium;
   (e) changing the temperature of the solution over time;
   (f) measuring the elevated gas pressure at predetermined intervals of time, the osmotic pressure being equal to the elevated pressure; and
   (g) calculating the changes in the osmotic pressure.

2. A method for monitoring changes in osmotic pressure of a sample as a function of time comprising the steps of:
   (a) placing a sample of a solution at an initial temperature into a sample cell above a membrane supported in the sample cell;
   (b) sealing the sample in the sample cell;
   (c) introducing gas at an elevated pressure to the sample cell to generate a dialyzate by allowing a portion of the solution to dialyze through the membrane and enter a transparent dialyzate exit tube connected to the sample cell;
   (d) varying the elevated pressure of the gas until equilibrium across the membrane is substantially achieved;
   (e) indicating osmotic equilibrium across the membrane with a substantially stationary dialyzate meniscus in the transparent dialyzate exit tube;
   (f) changing the temperature of the solution over time;
   (g) measuring the osmotic pressure at predetermined intervals of time; and
   (h) calculating the changes in the osmotic pressure.

3. A method as recited in claim 1 further comprising the step of:
   (a) suspending a starrier bar above the membrane; and
   (b) stirring the sample in the sample cell with the stirrer bar.

4. A method as recited in claim 2 further comprising the step of:
   (a) suspending a stirrer bar above the membrane; and
   (b) stirring the sample in the sample cell with the stirrer bar.

5. A method for monitoring changes in osmotic pressure of a sample as a function of time comprising the steps of:
   (a) placing a sample of a solution at an initial temperature into a sample cell above a membrane supported in the sample cell;
   (b) adding reactants to the sample;
   (c) sealing the sample and reactants in the sample cell;
   (d) introducing gas at an elevated pressure to the sample cell to generate a dialyzate by allowing a portion of the solution to dialyze through the membrane;
   (e) varying the elevated pressure of the gas until equilibrium across the membrane is substantially achieved, equilibrium being indicated by a substantially stationary dialyzate meniscus in a transparent dialyzate exit tube connected to the sample cell;
   (f) measuring the osmotic pressure at predetermined intervals of time; and
   (g) calculating the changes in the osmotic pressure.

6. A method as recited in claim 5 further comprising the step of:

(a) suspending a stirrer bar above the membrane; and (b) stirring the sample in the sample cell with the stirrer bar.

7. A method as recited in claim 5 further comprising the step of:

maintaining the sample at a constant temperature.

8. A method for monitoring changes in osmotic pressure of a sample as a function of time comprising the steps of:

(a) placing a sample of a solution at an initial temperature into a sample cell above a membrane supported in the sample cell;

(b) adding reactants to the sample;

(c) sealing the sample and reactants in the sample cell;

(d) introducing gas at an elevated pressure to the sample cell to generate a dialyzate by allowing a portion of the solution to dialyze through the membrane and enter a transparent dialyzate exit tube open to atmosphere and connected to sample cell;

(e) varying the elevated pressure of the gas to obtain a substantially stationary dialyzate meniscus visually observable in the transparent dialyzate exit tube, the substantially stationary dialyzate meniscus indicating osmotic equilibrium across the membrane;

(f) measuring the osmotic pressure at predetermined intervals of time; and (g) calculating the changes in the osmotic pressure.

9. A method as recited in claim 8 further comprising the step of:

(a) suspending a stirrer bar above the membrane; and (b) stirring the sample in the sample cell with the stirrer bar.

10. A method as recited in claim 8 further comprising the step of:

maintaining the sample at a constant temperature.

11. A method as recited in claim 1 wherein:

said measuring step is performed by reading a pressure gauge showing the elevated pressure of the gas that yielded the substantially stationary dialyzate meniscus, the elevated pressure of the gas being substantially equivalent to the osmotic pressure of the sample.

12. A method as recited in claim 11, said measuring step further comprising the step of:

performing a hydrostatic pressure correction based on the height of the solution in the sample cell in the height of the dialyzate in the dialyzate exit tube.

13. A method as recited in claim 2 wherein:

said measuring step is performed by reading a pressure gauge showing the elevated pressure of the gas that yielded the substantially stationary dialyzate meniscus, the elevated pressure of the gas being substantially equivalent to the osmotic pressure of the sample.

14. A method as recited in claim 13, said measuring step further comprising the step of:

performing a hydrostatic pressure correction based on the height of the solution in the sample cell in the height of the dialyzate in the dialyzate exit tube.

15. A method as recited in claim 5 wherein:

said measuring step is performed by reading a pressure gauge showing the elevated pressure of the gas that yielded the substantially stationary dialyzate meniscus, the elevated pressure of the gas being substantially equivalent to the osmotic pressure of the sample.

16. A method as recited in claim 15, said measuring step further comprising the step of:

performing a hydrostatic pressure correction based on the height of the solution in the sample cell in the height of the dialyzate in the dialyzate exit tube.

17. A method as recited in claim 8 wherein:

said measuring step is performed by reading a pressure gauge showing the elevated pressure of the gas that yielded the substantially stationary dialyzate meniscus, the elevated pressure of the gas being substantially equivalent to the osmotic pressure of the sample.

18. A method as recited in claim 17, said measuring step further comprising the step of:

performing a hydrostatic pressure correction based on the height of the solution in the sample cell in the height of the dialyzate in the dialyzate exit tube.

19. A method as recited in claim 1 further comprising the step of:

collecting the dialyzate passing through the membrane in a dialyzate collector and flowing the dialyzate therefrom to the transparent dialyzate exit tube.

20. A method as recited in claim 1 further comprising the step of:

collecting the dialyzate passing through the membrane in a meandering dialyzate cell and flowing the dialyzate therefrom to the transparent dialyzate exit tube.

21. A method as recited in claim 8 further comprising the step of:

collecting the dialyzate passing through the membrane in a dialyzate collector and flowing the dialyzate therefrom to the transparent dialyzate exit tube.

22. A method as recited in claim 8 further comprising the step of:

collecting the dialyzate passing through the membrane in a meandering dialyzate cell and flowing the dialyzate therefrom to the transparent dialyzate exit tube.

* * * * *